United States Patent [19]

Green et al.

[11] Patent Number: 5,501,689
[45] Date of Patent: Mar. 26, 1996

[54] PLAQUE STAPLER

[75] Inventors: David T. Green, Westport; Henry Bolanos, Norwalk; Daniel E. Alesi, Sherman, all of Conn.; Kenneth E. Toso, Portchester, N.Y.

[73] Assignee: United States Surgical Corporation, Norwalk, Conn.

[21] Appl. No.: 191,230

[22] Filed: Feb. 3, 1994

[51] Int. Cl.⁶ .................................................. A61B 17/04
[52] U.S. Cl. ........................... 606/139; 606/153; 227/19; 227/175
[58] Field of Search ........................... 606/219, 139–148; 227/19, 175–181

[56]         References Cited

U.S. PATENT DOCUMENTS

| 2,301,622 | 11/1942 | Hembrecht . |
| 3,351,191 | 11/1967 | Mallina . |
| 3,366,301 | 1/1968 | Mallina . |
| 3,489,330 | 1/1970 | Mallina et al. . |
| 3,575,038 | 4/1971 | Mallett . |
| 3,606,888 | 9/1971 | Wilkinson . |
| 3,873,016 | 3/1975 | Fishbein . |
| 4,111,206 | 9/1978 | Vishnevsky et al. . |
| 4,196,836 | 4/1980 | Becht ........................ 227/19 |
| 4,470,532 | 9/1984 | Froehlich .................. 227/19 |
| 4,664,305 | 5/1987 | Blake, III et al. ......... 227/19 |
| 4,930,674 | 6/1990 | Barak ........................ 227/19 |
| 5,188,638 | 2/1993 | Tzakis ...................... 606/153 |
| 5,337,937 | 8/1994 | Remiszewski et al. ... 227/19 |

FOREIGN PATENT DOCUMENTS

| 786605 | 6/1968 | Canada . |
| 939929 | 10/1963 | United Kingdom . |

*Primary Examiner*—Gary Jackson

[57]              ABSTRACT

An apparatus for stapling the plaque lining of an artery or vein to the wall of the artery or vein, which comprises first and second opposed cooperative elongated members pivotably associated with one another. The first and second elongated members have distal ends, and proximal ends forming handles. The first elongated member forms an anvil portion at its distal end which is configured for placement into an open end of a vein and/or an artery. A staple cartridge assembly is disposed on the distal end of the second elongated member and includes a staple magazine containing a multiplicity of staples longitudinally and sequentially aligned with the staple magazine. Actuating means are provided which are supported by the staple cartridge assembly for movement in a given direction therealong to drive the staples in the staple magazine toward a staple exit end.

7 Claims, 4 Drawing Sheets

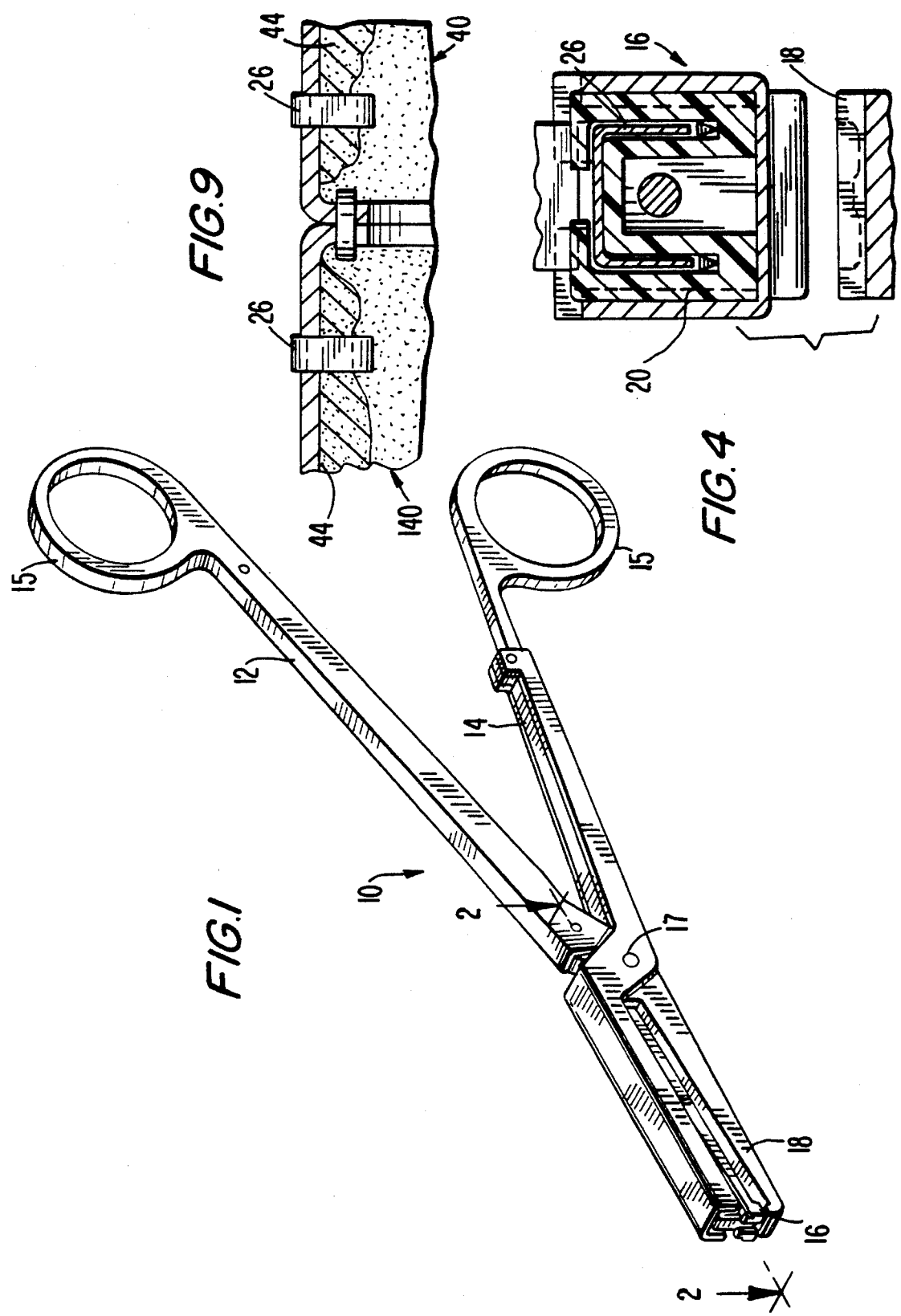

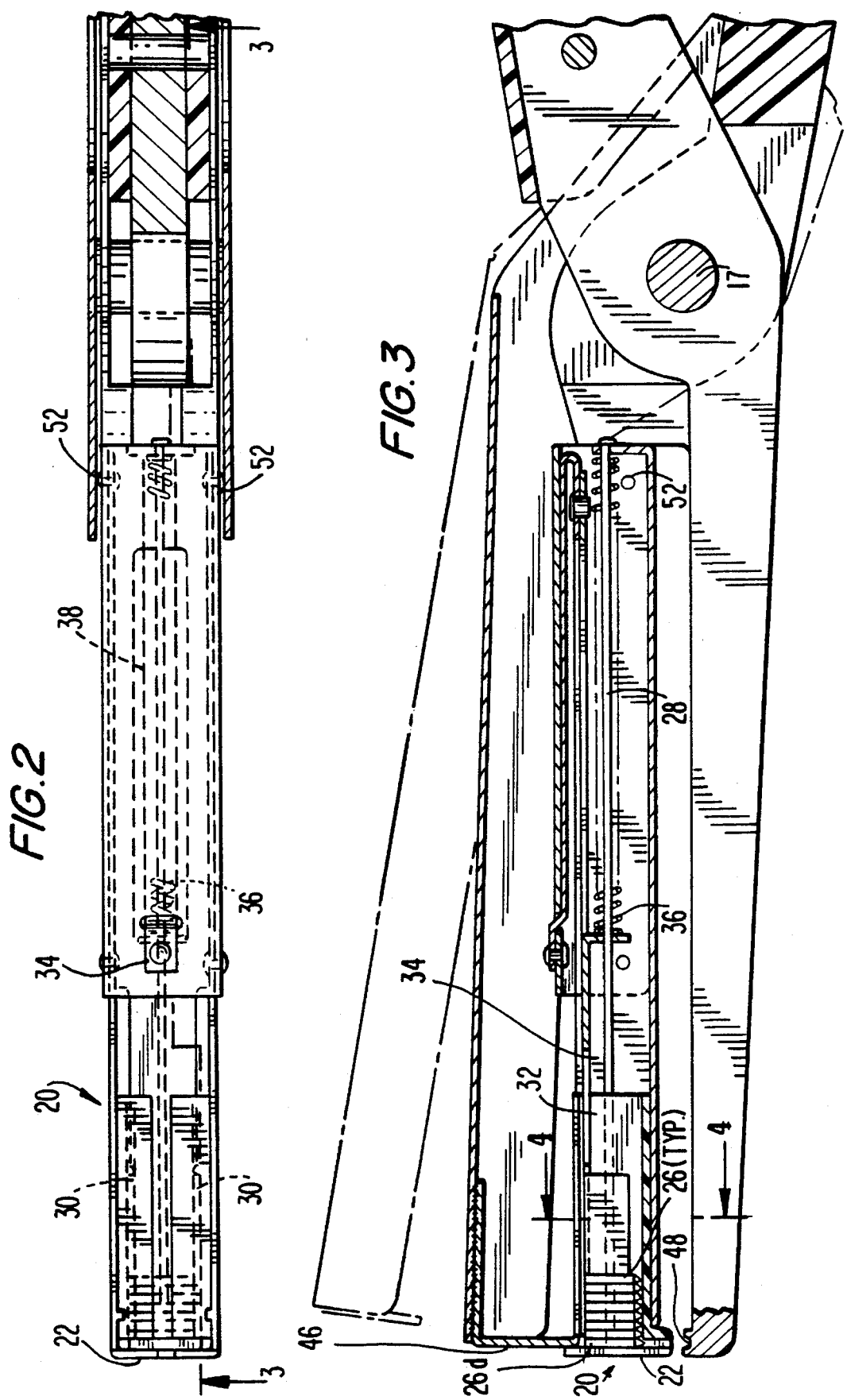

5,501,689

PLAQUE STAPLER

BACKGROUND OF THE INVENTION

1. Field of the Invention

This invention relates to an apparatus and method for use in conjunction with vascular anastomosis and more particularly to a stapler for stapling plaque lining the inside of a blood vessel to the wall of the blood vessel.

2. Description of the Related Art

Procedures involving the joining of hollow body organs, or more particularly, vascular anastomosis, are well known surgical procedures. Typically, in performing vascular anastomosis, the vascular tissue, e.g., artery or vein, to be joined is clamped by a circular anastomosis stapling instrument between an anvil assembly and a staple holding assembly, both of which are located at the distal end of the instrument. The clamped tissue is then stapled by driving staples from the staple holding assembly through the tissue and into contact with the anvil assembly which clinches the staples.

Plaque lining the artery or vein is typically encountered by the surgeon prior to performing the above-described anastomosis procedure. Plaque, built up on the walls of the artery or vein, is a hard material which interferes with the anastomosis procedure in a number of ways. One manner in which the plaque inhibits the surgeon is the plaque's resistance to staple penetration. A greater problem associated with the plaque is the possibility that a piece of the plaque may break loose during the anastomosis procedure, for instance, when the staples contact the plaque. A loose piece of plaque transferred in the blood stream can result in an embolism.

Instruments and methods of using same have been developed which are capable of stapling through tough and hard tissue, however these devices generally have not included an anvil or stapling assembly which is configured for insertion into a vein or artery. Those instruments which are capable of performing in the above described environment, typically are complex and expensive to manufacture. A need in the art therefore exists for an improved stapling apparatus capable of stapling arterial and vascular plaque to the artery or vein which minimizes the likelihood of a piece of plaque being broken off.

SUMMARY OF THE INVENTION

An apparatus is disclosed for stapling the plaque lining of an artery or vein to the wall of the artery or vein, which comprises first and second opposed cooperative elongated members pivotably associated with one another. The first and second elongated members have distal ends and proximal ends. The proximal ends form handles. The elongated members are pivotably associated with one another at a location between the distal and proximal ends. The first elongated member forms an anvil portion at its distal end which is configured for placement into an open end of a vein and/or an artery. The anvil has a staple clinching groove.

The apparatus further includes a staple cartridge assembly disposed on the distal end of the second elongated member. The staple cartridge assembly has a staple magazine containing a multiplicity of staples longitudinally and sequentially aligned with the staple magazine. The staple cartridge assembly has a distal end and a proximal end. The staple magazine has a staple load end and a staple exit end. Actuating means are also included in the apparatus and are supported by the staple cartridge assembly for movement in a given direction therealong to drive the staples in the staple magazine toward the staple exit end.

BRIEF DESCRIPTION OF THE DRAWINGS

FIG. 1 is a perspective view of one embodiment of a preferred plaque stapler in accordance with the present invention;

FIG. 2 is a partial top view of the top handle member of the present invention taken along line 2—2 of FIG. 1 illustrating the anvil assembly of the top handle member;

FIG. 3 is a partial side view of the plaque stapler of the present invention taken along line 3—3 of FIG. 2 illustrating the distal end of the plaque stapler;

FIG. 4 is a cross-sectional view taken along line 4—4 of FIG. 3 illustrating the distal end of the plaque stapler;

FIG. 9 is a cross-sectional view of an anastomosed vein or artery;

DETAILED DESCRIPTION OF THE PREFERRED EMBODIMENTS

Figure 5:
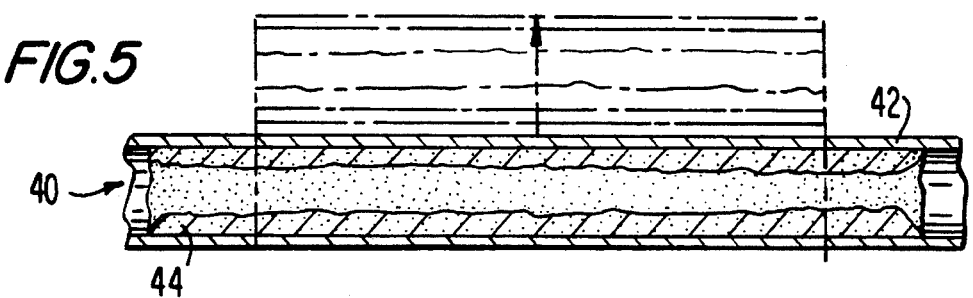
FIG. 5 is a partial cross-sectional view of an artery or vein illustrating plaque lining the artery or vein.

In the drawings like reference numerals identify similar or identical elements throughout the several views. In addition, while the following description is directed toward and apparatus and method for stapling vascular or arterial plaque to veins or arteries, it will be appreciated to those having ordinary skill in the art that the present invention may be used to staple other tissue as well. In the description which follows, the term "distal" refers to a direction of the apparatus away from the user and towards the patient's body tissue while the term "proximal" refers to a direction towards the user and away from the patient's body tissue.

Referring to FIG. 1, plaque stapler 10 of the present invention includes an elongated top handle member 12 and an elongated bottom handle member 14 each of which has finger rings 15 formed at their proximal ends. The distal end of bottom handle member contains staple cartridge assembly 16 and staple driving member 46. Disposed opposite staple cartridge assembly 16 on the distal end of top handle member 12 is anvil portion 18. Top handle member 12 and bottom handle member 14 are pivotably connected with one another by transverse pivot pin 17 disposed proximal to staple cartridge 16 and anvil portion 18.

As can be seen in FIGS. 2–4, staple cartridge assembly 16 is movable with respect to bottom handle member 14 and staple driving member 46, for example, by means of pivot pins 52 passing through apertures in cartridge assembly 16 corresponding to apertures in bottom handle member 14 includes staple magazine 20 having a staple exit end 22 and a staple load end 24. Staples 26 are contained within staple magazine 20 along staple receiving channel 30. Support rod 28 connected at its distal end to staple magazine 20 and at its proximal end to the proximal end of staple cartridge assembly 16, maintains the position of staple magazine 20. Pusher element 32, positioned distal and adjacent to staples 26 within staple receiving channel 30, is slidably disposed within staple receiving channel 30. Pusher element 32 is biased towards staple exit end 22 by pressure from actuating rod 34 connected to the proximal end of pusher element 32. Actuating rod 34 is slidably disposed within staple cartridge assembly 16 and is connected at its proximal end to the distal end of feed spring 36 which provides biasing pressure against actuating rod 34 towards staple exit end 22. Feed spring 36 is disposed around support rod 28 and connected at its proximal end to the proximal end of staple cartridge assembly 16. Feed spring cover 38 (shown in phantom in FIG. 2), disposed over feed spring 36 prevents foreign material from interfering with feed spring 36.

Figure 6:
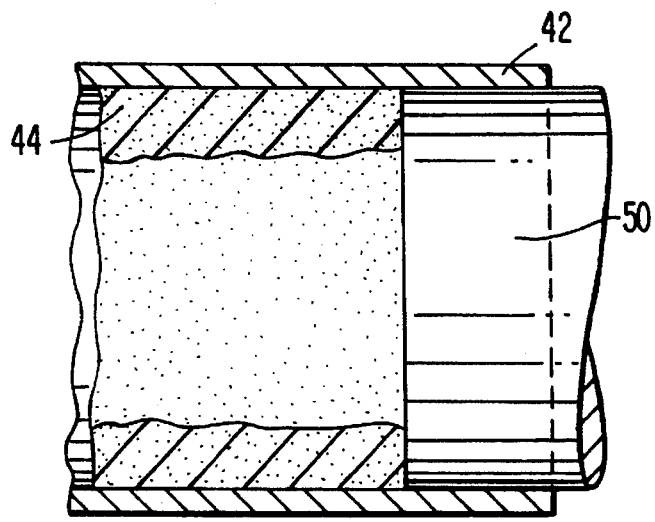
FIG. 6 is a enlarged view of the vein or artery of FIG. 5 illustrating the removal of plaque by a circular knife.

Prior to the introduction of plaque stapler 10 into the patient, the operator will preferably first remove a portion of plaque from the ends of the respective vein segments to be joined. Referring to FIG. 6, the removal of the plaque lining 44 from vein wall 42 can be accomplished with known surgical procedures and instruments, for example circular knife 50. The vein segments, with plaque removed therefrom, are placed in condition for introduction of plaque stapler 10.

Referring once again to FIG. 1, plaque stapler 10 is placed in a open position by directing finger rings 15 away from one another simultaneously causing staple cartridge assembly 16 and anvil portion 18 to be directed away from one another. When cartridge assembly 16 and anvil portion 18 are sufficiently spaced from one another, the selected artery or vein, for example, a vein, is positioned between staple cartridge assembly 16 and anvil portion 18 by inserting anvil portion 18 into the vein while staple cartridge assembly 16 remains outside of the vein.

Referring now to FIGS. 5–8, vein 40 is clinched between staple cartridge 16 and anvil portion 18 upon the squeezing of finger rings 15 toward one another. This causes staple cartridge assembly 16 and anvil portion 18 to be directed toward one another. This puts staple cartridge assembly 16 into contact with vein wall 42, and puts anvil portion 18 into contact with plaque lining 44.

Following the clinching of vein 40, further squeezing of finger rings 15 toward one another forces staple driving member 46 of bottom handle member 14 into contact with the most distal staple 26d located at staple exit end 22 of staple magazine 20 (see FIG. 3). Referring once again to FIGS. 5–9, still further squeezing of finger rings 15 causes staple driving member 46 to propel staple 26d. Staple 26d punctures vein wall 42 and plaque lining 44 with the tips thereof. Staple 26d then contacts anvil recess 48 thereby bending the tips of staple 26d and firmly connecting plaque lining 44 to vein wall 42.

Referring once again to FIG. 3, following the stapling of vein 40, plaque stapler is reset when staple cartridge assembly 16 and anvil portion 18 are directed away from one another. This removes staple driving member 46 from staple magazine 20, and allows a new staple 26d to be advanced by pusher element 32 into firing position at staple exit end 22.

Figure 7:
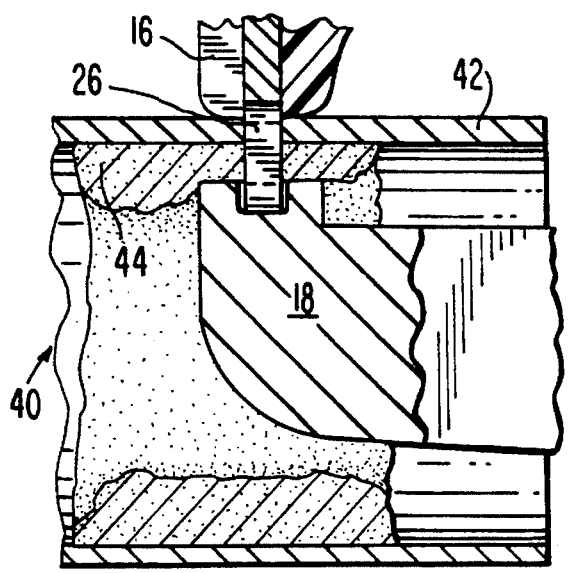
FIG. 7 is a view similar to that of FIG. 6 illustrating the stapling of plaque to the inner wall lining of the artery or vein.
Figure 8:
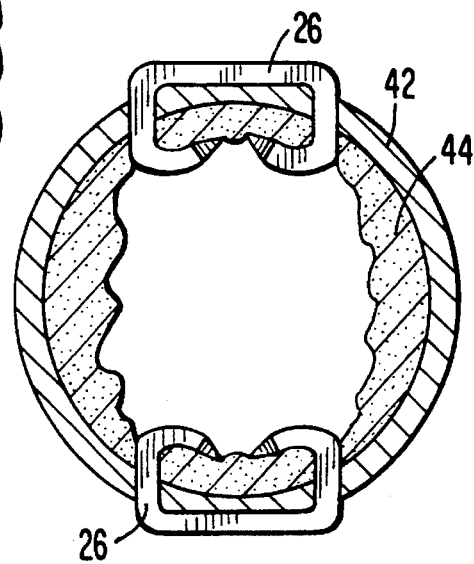
FIG. 8 is a cross-sectional view of a vein or artery with the plaque stapled to inner wall lining after stapling per FIG. 7.

The above stapling operation can now be repeated with respect to plaque opposite that of the previously stapled plaque as shown in FIG. 7. Thus the plaque lining 44 is firmly secured to vein wall 42 in this segment of vein 40. Similarly a segment of a second vein 140 stapled. Then the two vein segments are placed in condition for joining by known anastomosis procedure (See FIG. 9). Accordingly, such anastomosis may be accomplished while minimizing interference from plaque and minimizing concern of pieces of plaque breaking away and falling into the blood stream of the patient.

Figure 10:
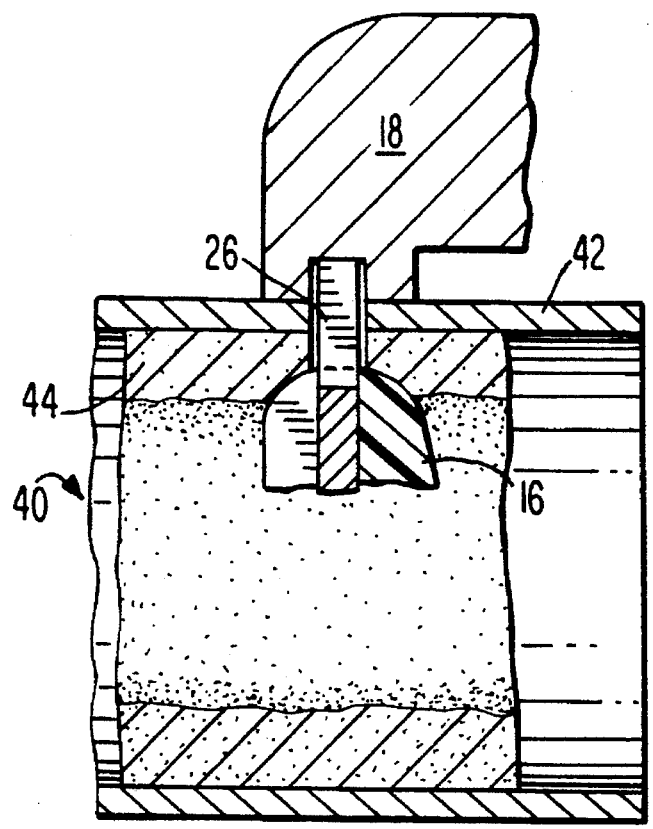
FIG. 10 is a view similar to that of FIG. 7 but illustrating firing staples from inside the vein or artery.
Figure 11:
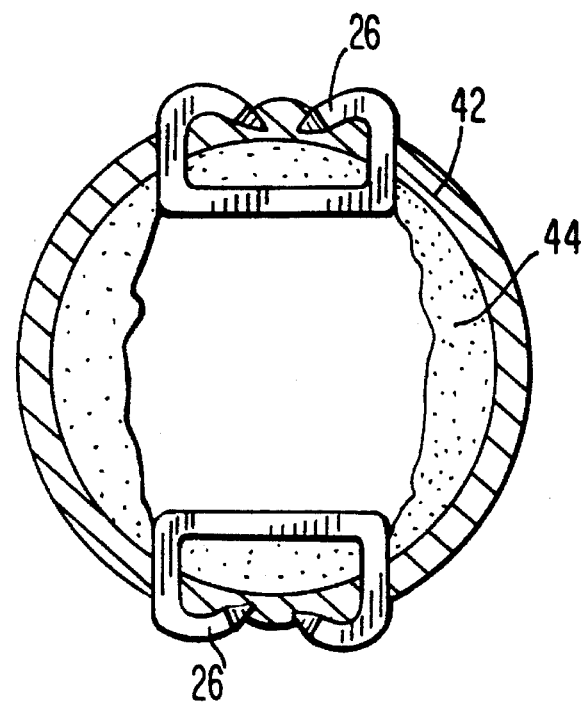
FIG. 11 is a cross-section view of a vein or artery with the plaque stapled to the inner wall lining after firing the staples per FIG. 10.

FIG. 10 shows firing the staples 26 from inside the vein wall 26. FIG. 11 shows the staples 26 after firing per FIG. 10. The staples 26 may be fired from inside the vein wall 42 where the size of the vein permits.

In as much as the present invention is subject to many variations, modifications and changes in detail, the subject matter discussed above and shown in the accompanying drawings is intended to be illustrative only and not to be taken in a limiting sense.

What is claimed is:

1. A method for joining first and second plaque-lined blood vessel segments to one another, comprising the steps of:

a) detaching a portion of plaque lining from adjacent end portions of the first and second blood vessel segments to be joined;

b) providing a surgical stapling device including an anvil for placement adjacent an interior surface of the first and second vessel segments and a cartridge assembly containing a plurality of staples for placement adjacent an exterior surface of the first and second vessel segments and structure for driving the staples from the cartridge through the plaque lining the walls of the blood vessels to be formed against the anvil;

c) stapling the remaining portion of the plaque lining in each blood vessel segment to a wall thereof; and d) joining the end portions of the blood vessel segments to one another in the area from which the plaque lining has been removed.

2. The method of claim 1, wherein said stapling step comprising:

placing into an open end of said first blood vessel segment an apparatus comprising first and second opposed cooperative elongated members pivotably associated with one another, said first and second elongated members having distal ends and proximal ends, said proximal ends forming handles;

pivoting said elongated members relative to one another at a location between said distal and proximal ends;

discharging a staple from said cartridge assembly disposed on the distal end of said second elongated member into a staple clinching groove of said anvil formed on a distal end of said first elongated member, said distal end of said first elongated member configured for placement into said open end of said first blood vessel segment;

said staple cartridge assembly having a staple magazine containing a multiplicity of staples longitudinally and sequentially aligned with said staple magazine, said staple cartridge assembly having a distal end and a proximal end, said staple magazine having a staple load end and a staple exit end; and moving actuating means supported by said staple cartridge assembly in a given direction therealong to drive said staples in said staple magazine toward said staple exit end.

3. The method according to claim 2, wherein said plaque stapling step is accomplished by placing said anvil portion of said first elongated member into the open end of the first blood vessel segment while positioning said staple cartridge assembly outside the first blood vessel segment, clinching the first blood vessel segment between said anvil portion and said cartridge assembly, further clinching the vein or artery causing a staple contained in said staple magazine to be driven by said actuating means through the wall of said first blood vessel segment and through said plaque lining and into contact with said staple clinching groove.

4. The method of claim 3, further comprising repeating said stapling steps performed on said first blood vessel segment on said second blood vessel segment.

5. A method for joining first and second plaque-lined blood vessel segments to one another comprising the steps of:

a) clearing a portion of plaque lining from adjacent end portions of the first and second blood vessel segments to be joined;

b) providing a surgical fastening device including an anvil for placement adjacent an interior surface of the first and second vessel segments and a cartridge assembly containing a plurality of fasteners for placement adjacent an exterior surface of the first and second vessel segments and structure for driving the fasteners from the cartridge through the plaque lining the walls of the blood vessels to be formed against the anvil;

c) fastening the remaining portion of the plaque lining in each of the blood vessel segments to the walls thereof; and d) joining the end portion of the blood vessel segments to one another in the area from which the plaque lining has been cleared.

6. A method according to claim 5, wherein the step of fastening a portion of the plaque lining comprises stapling the plaque lining to the wall of the blood vessel segment.

7. A method according to claim 5, wherein the step of joining the end portions of the blood vessel segments comprises stapling the blood vessel segments to one another.

* * * * *